US00PP34237P2

(12) United States Plant Patent
Bradford et al.

(10) Patent No.: US PP34,237 P2
(45) Date of Patent: May 17, 2022

(54) NECTARINE TREE NAMED 'GIANT SUGARINE'

(50) Latin Name: *Prunus persica*
Varietal Denomination: Giant Sugarine

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 0 days.

(21) Appl. No.: 17/300,911

(22) Filed: Dec. 17, 2021

(51) Int. Cl.
*A01H 5/08* (2018.01)
*A01H 6/74* (2018.01)

(52) U.S. Cl.
USPC ..... Plt./190

(58) Field of Classification Search
USPC ..... Plt./187, 190
See application file for complete search history.

(56) References Cited

U.S. PATENT DOCUMENTS

PP14,240 P2 10/2003 Bradford
PP18,752 P2 4/2008 Bradford

*Primary Examiner* — Susan McCormick Ewoldt

(57) ABSTRACT

The present invention relates to a new and distinct variety of nectarine tree, *Prunus persica*, broadly characterized by a medium size, vigorous, hardy, self-fertile, productive and regular bearing tree. The variety has a small non-showy blossom and blooms during the early season, with a chilling requirement of about 400 hours. The fruit matures under the ecological conditions described in early June, with first picking on Jun. 8, 2021. The fruit is uniform, large in size for an early season variety, sub-acidic and sweet in flavor, fairly globose in shape, clingstone in type, firm in texture, yellow in flesh color, and full red in skin color.

1 Drawing Sheet

Botanical classification: *Prunus persica.*
Variety denomination: 'GIANT SUGARINE'.

BACKGROUND OF THE VARIETY

In a continuing effort to improve the quality of shipping fruits, we, the inventors, typically hybridize a large number of peach, nectarine, plum, apricot, and cherry seedlings each year. We also grow a smaller number of open pollinated seeds of each of these fruits, usually to capture recessive traits. The present invention relates to a new and distinct variety of nectarine tree, which has been denominated varietally as 'Giant Sugarine'.

The present variety was hybridized by us in 2008 as a first generation cross using 'Giant Pearl' (U.S. Plant Pat. No. 14,240) nectarine as the selected seed parent and 'OP373' (unpatented) nectarine as the selected pollen parent. Upon reaching maturity the fruit of this hybridization was gathered, and the seeds were removed, cracked, stratified, germinated, and grown as seedlings on their own root in our greenhouse facility. Upon reaching dormancy we transplanted them to a cultivated area of our experimental orchard located near Le Grand, Calif., in Merced County (San Joaquin Valley). During the fruit evaluation season of 2012 we selected the present variety as a single tree from the group of seedlings described above. Subsequent to origination of the present variety of nectarine tree, we asexually reproduced it by budding and grafting in the experimental orchard described above, and such reproduction of plant and fruit characteristics were true to the original tree in all respects. The reproduction of the variety included the use of 'Nemaguard' (unpatented) rootstock upon which the present variety was compatible and true to type.

The present variety is similar to its seed parent, 'Giant Pearl' (U.S. Plant Pat. No. 14,240) nectarine by having a medium size tree, by being vigorous, by being self-fertile, by having a small blossom, by having reniform leaf glands, and by producing nectarines that are large in size, that are clingstone in type, and that are sub-acidic in flavor, but is quite distinguished from it by producing nectarines that are yellow instead of white in flesh color, that are a much fuller and darker red in skin color, and that ripen about seventy days earlier.

The present variety is similar to its pollen parent, 'OP373' (unpatented) nectarine, by being self-fertile and by producing nectarines that are yellow in flesh color, and clingstone in type, but is quite distinguished from it by producing fruit that is larger in size, that is sub-acidic instead of acidic in flavor, that is firmer in texture, and that ripens about two weeks later.

The present variety is most similar to 'June Sweet' (U.S. Plant Pat. No. 18,752) nectarine by being self-fertile, by having reniform leaf glands, by having a bitter kernel and by producing nectarines that are yellow in flesh color, clingstone in type, firm in texture, fairly globose in shape, and sub-acidic and sweet in flavor, but is distinguished therefrom by blooming earlier, by requiring less chilling hours, by having a small non-showy instead of large showy blossom and by producing nectarines that are larger in size, darker red in skin color, and that mature about six days earlier.

SUMMARY OF VARIETY

In summary, the present nectarine variety is characterized by a medium size, vigorous, hardy, self-fertile, productive and regular bearing tree. The variety has a small non-showy blossom and blooms during the early season, with a chilling requirement of about 400 hours. The fruit matures under the ecological conditions described in early June, with first picking on Jun. 8, 2021. The fruit is uniform, large in size for an early season variety, sub-acidic and sweet in flavor, fairly globose in shape, clingstone in type, firm in texture, yellow in flesh color, and full red in skin color.

DRAWING

The accompanying photograph consists of four whole fruits positioned to display the characteristics of the skin color and form, one divided fruit to reveal the flesh and stone, a tip shoot of new leaf growth, typical leaves, and two insets depicting the flower buds and blossoms as they appear on the tree during the blooming season.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Jun. 14, 2021, on the original tree during its thirteenth growing season. The blossom and flower descriptions were made the previous blooming season. All major color code designations are by reference to the Inter-Society Color Council, National Bureau of Standards. Common color names are also used occasionally.

PARENTAGE

Seed parent: 'Giant Pearl' (U.S. Plant Pat. No. 14,240) nectarine.

Pollen parent: 'OP373' (unpatented) nectarine.

TREE

Size: Medium, reaching and maintaining a height of 9' [2.74 m.] and a spread of 10' [3.05 m.] after thirteen growing seasons utilizing typical dormant pruning.

Vigor: Vigorous, responding about average to irrigation and fertilization. The variety grows about 2' [0.61 m.] of surplus top-growth during the spring and summer. The plant should be grown on a standard commercial rootstock for production purposes.

Growth: Spreading and dense.

Form: Pruned to a vase shape.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning usually necessary.

Fertility: Self-fertile.

Bearing: Regular bearer, with no crop failures observed.

Chilling requirement: About 400 hours.

Leaf bud burst: Medium, during the middle of flowering.

Trunk:

*Size*.—Medium, reaching a maximum diameter of 6¼" [158.8 mm.] after the thirteenth growing season.

*Texture*.—Medium to shaggy.

*Bark color*.—A Light brownish gray [63. l.brGy] and Grayish brown [61. gy.Br] variegation with Dark grayish brown [62. d.gy.Br] crevices present.

*Lenticels*.—Approximate Number Per Square Inch: 8. Color: Grayish yellowish brown [80. gy.yBr]. Average Size: ⅜" [9.5 mm.] in length. The width is typically one fourth as much as the length. Shape: Elongated.

Branches:

*Size*.—Medium, diameter of main scaffold is 3" [76.2 mm.] measured 12" above the crotch, diameter of limb is 1⅜" [34.9 mm.] measured 12" above the first fork.

*Texture*.—Smooth to medium on first and second year wood, increasing in roughness with age.

*Color*.—1st Year Wood Topside: Grayish red [19. gy.R]. 1st Year Wood Underside: Brilliant yellow green [116. brill.YG]. Older Wood: A Strong brown [55. s.Br] and Moderate brown [58. m.Br] variegation with Grayish brown [61. gy.Br] crevices present.

*Lenticels*.—Number Per Square Inch: About 35 on second year wood. Color: Strong yellowish brown [74. s.yBr]. Average Size: Small, 1/16" [1.6 mm.] in length. The width is typically one fourth as much as the length. Shape: Elongated.

Leaves:

*Size*.—Large to medium. Average Length: 5½" [139.7 mm.]. Average Width: 1½" [38.1 mm.].

*Arrangement*.—Alternate.

*Thickness*.—Medium.

*Form*.—Elliptical.

*Apex*.—Acuminate.

*Base*.—Acute with an average sixty-five degree angle.

*Surface*.—Smooth on both sides.

*Color*.—Dorsal Surface: Moderate olive green [125. m.OlG]. Ventral Surface: Moderate yellow green [120. m.YG].

*Red midvein*.—Absent.

*Margin*.—Finely serrate.

*Venation*.—Pinnately net veined.

*Petiole*.—Average Length: 7/16" [11.1 mm.]. Average Thickness: 1/16" [1.6 mm.]. Color: Strong yellow green [117. s.YG].

*Stipules*.—Number: 2 per leaf, up to 6 per growing tip. Average Length: ¼" [6.4 mm.]. Color: Vivid yellow green [115. v.YG] becoming Moderate brown [58. m.Br] with age.

*Glands*.—Number: 2 to 4 per leaf. Position: Alternate, first pair is located at the intersection of petiole and base of blade. Form: Reniform. Size: Medium, about 1/32" [0.8 mm.] in length, about 1/64" [0.4 mm.] in width. Color: Strong yellow green [117. s.YG].

*Leaf buds*.—Pointed.

Flower buds:

*Hardiness*.—Hardy, with respect to central California blooming season.

*Diameter*.—Typically ⅜" [9.5 mm.] 1 week before bloom.

*Length*.—Typically ⅝" [15.9 mm.] 1 week before bloom.

*Form*.—Not appressed.

*Surface*.—Pubescent.

*Tip color*.—Strong purplish pink [247. s.pPk] with anthers usually protruding.

Flowers: Perfect, complete, perigynous, usually a single pistil, about thirty stamens, five sepal and petal locations alternately positioned.

*Type*.—Non-showy, small.

*Average flower diameter*.—1⅛" [28.6 mm.].

*Average flower depth*.—5/16" [7.9 mm.] when fully open.

*Average pedicel length*.—⅛" [3.2 mm.].

*Number of petals*.—Mostly five, extra petal fragments occasionally observed, double blossoms not observed.

*Petal arrangement*.—Non-overlapping.

*Petal shape*.—Obovate.

*Petal margin*.—Entire, somewhat wavy.

*Average petal diameter*.—⅜" [9.5 mm.].

*Average petal length*.—⅝" [15.9 mm.].

*Petal apex*.—Rounded.

*Petal base*.—Rounded to somewhat acute.

*Petal color*.—Light purplish pink [249. l.pPk] toward the apex, Strong purplish red [255. s.pR] toward the base on both sides.

*Anther color*.—Strong yellowish pink [26. s.yPk] surrounding a Brilliant yellow [83. brill.Y] center at bloom onset.

*Pollen*.—Anthers produce an abundance of Brilliant yellow [83. brill.Y] pollen.

*Stigma color*.—Light greenish yellow [101. l.gY].

*Stigma position*.—Typically located about even with the nearby anthers.

*Stamen position*.—Typically located about 1/16" [1.6 mm.] below the petals.

*Average pistil length*.—11/16" [17.5 mm.].

*Average stamen length*.—7/16" [11.1 mm.].

*Ovary*.—Non-pubescent.

*Sepal color*.—Dark purplish red [259. d.pR] on the outer surface. The inner surface is a somewhat translucent Pinkish white [9. pkWhite] with both Grayish purplish red [262. gy.pR] and Vivid yellow green [115. v.YG] areas visible.

*Sepal length*.—¼" [6.4 mm.].

*Sepal width*.—3/16" [4.8 mm.].

*Sepal apex*.—Rounded to elliptical to match the sepal length and width.

*Sepal margin*.—Fairly smooth.

*Sepal outer surface*.—Pubescent.

*Fragrance*.—Moderate.

*Blooming period*.—Early compared to other varieties, blooms about 4 days before 'May Bright' (U.S. Plant Pat. No. 21,928) nectarine.

*Onset of bloom*.—One percent on Feb. 8, 2021.

*Date of full bloom*.—Feb. 20, 2021.

*Duration of bloom*.—One to two weeks, dependent on ambient temperature.

*Bloom density*.—Heavy.

*Number per cluster*.—1 to 3 with single flowers most common.

FRUIT

Maturity when described: Firm ripe, Jun. 14, 2021.

Date of first picking: Jun. 8, 2021.

Date of last picking: Jun. 18, 2021.

Size: Uniform, medium.

*Average diameter axially*.—3" [76.2 mm.].

*Average diameter across suture plane*.—3 1/16" [77.8 mm.].

*Average diameter across cheek plane*.—3" [76.2 mm.].

*Typical weight*.—8.4 ounces [238 grams].

Form: Uniform, globose, some slightly asymmetrical.

*Longitudinal section form*.—Round to slightly oblate.

*Axial view*.—Round.

Suture: Extends from the base to about ½" [12.7 mm.] beyond the pistil point.

*Near the base*.—A shallow groove.

*Along the side*.—A shallow trough.

*Near the apex*.—A moderate groove that rounds to a shallow trough past the apex.

Ventral surface: Rounded, lipped throughout, stronger lipping on one side.

Lips: Mostly unequal.

Cavity: Flaring with Light yellow [86. l.Y] stem markings present.

*Depth*.—7/16" [11.1 mm.].

*Breadth*.—1 5/16" [33.3 mm.].

Base: Truncate.

Apex: Rounded, cordate if viewed parallel to the suture.

Pistil point: Apical, negligible in length, depressed within the suture.

Stem: Medium.

*Average length*.—⅜" [9.5 mm.].

*Average width*.—3/16" [4.8 mm.].

Skin:

*Thickness*.—Medium.

*Surface*.—Smooth.

*Tenacity*.—Tenacious to the flesh.

*Astringency*.—Non-astringent.

*Tendency to crack*.—None observed.

*Color*.—Very deep red [14. v.deep R] over a Dark red [16. d.R] background with virtually no freckling.

Flesh:

*Color*.—Vivid yellow [82. v.Y] with a slight amount of Strong red [12. s.R] streaking and flecking present.

*Surface of pit cavity*.—Covered with Brilliant yellow [83. brill.Y] broken fibers when twisted away from the stone.

*Amygdalin*.—Scarce.

*Juice*.—Moderate.

*Texture*.—Firm, crisp.

*Fibers*.—Abundant, fine, tender.

*Ripens*.—Fairly even, slightly earlier toward the apex.

*Flavor*.—Sub-acidic, sweet, typically 15 brix.

*Aroma*.—Wanting.

*Eating quality*.—Very good.

STONE

Type: Clingstone.

Form: Oval.

Hilum: Narrow, oval.

Base: Rounded.

Apex: Acute.

Sides: Mostly equal.

Tip: Acute, typically ⅛" [3.2 mm.] in length.

Surface: Irregularly furrowed toward the apex, pitted toward the base.

Ridges: Jagged.

External color: Dark orange yellow [72. d.OY] when first removed.
Pit wall color when cracked: Pale orange yellow [73. p.OY].
Cavity surface color: Light orange yellow [70. l.OY].
Average pit wall thickness: 3/16" [4.8 mm.].
Average length: 1¼" [31.8 mm.].
Average width: 1⅛" [28.6 mm.].
Average breadth: ¾" [19.1 mm.].
Tendency to split: None observed.
Kernel:
*Form*.—Oval.
*Skin color*.—Light yellow [86. l.Y].
*Pellicle color*.—Dark brown [59. d.Br].
Vein color.—Brilliant yellow [83. brill.Y].
*Taste*.—Slightly bitter.
*Viable*.—Yes.
*Average length*.—¾" [19.1 mm.].
*Average width*.—½" [12.7 mm.].
*Amygdalin*.—Slight.

USE

Market: Fresh market and long distance shipping.
Keeping quality: Good, fruit quality observed to remain in good condition after 17 days in standard cold room at 36° Fahrenheit [2° Celsius].
Shipping quality: Good.
Resistance to insects: Not tested.
Resistance to diseases: Not tested.

OTHER NOTES

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described, that is most similar to 'June Sweet' (U.S. Plant Pat. No. 18,752) nectarine by being self-fertile, by having reniform leaf glands, by having a bitter kernel and by producing nectarines that are yellow in flesh color, clingstone in type, firm in texture, fairly globose in shape, and sub-acidic and sweet in flavor, but is distinguished therefrom by blooming earlier, by requiring less chilling hours, by having a small non-showy instead of large showy blossom and by producing nectarines that are larger in size, darker red in skin color, and that mature about six days earlier.

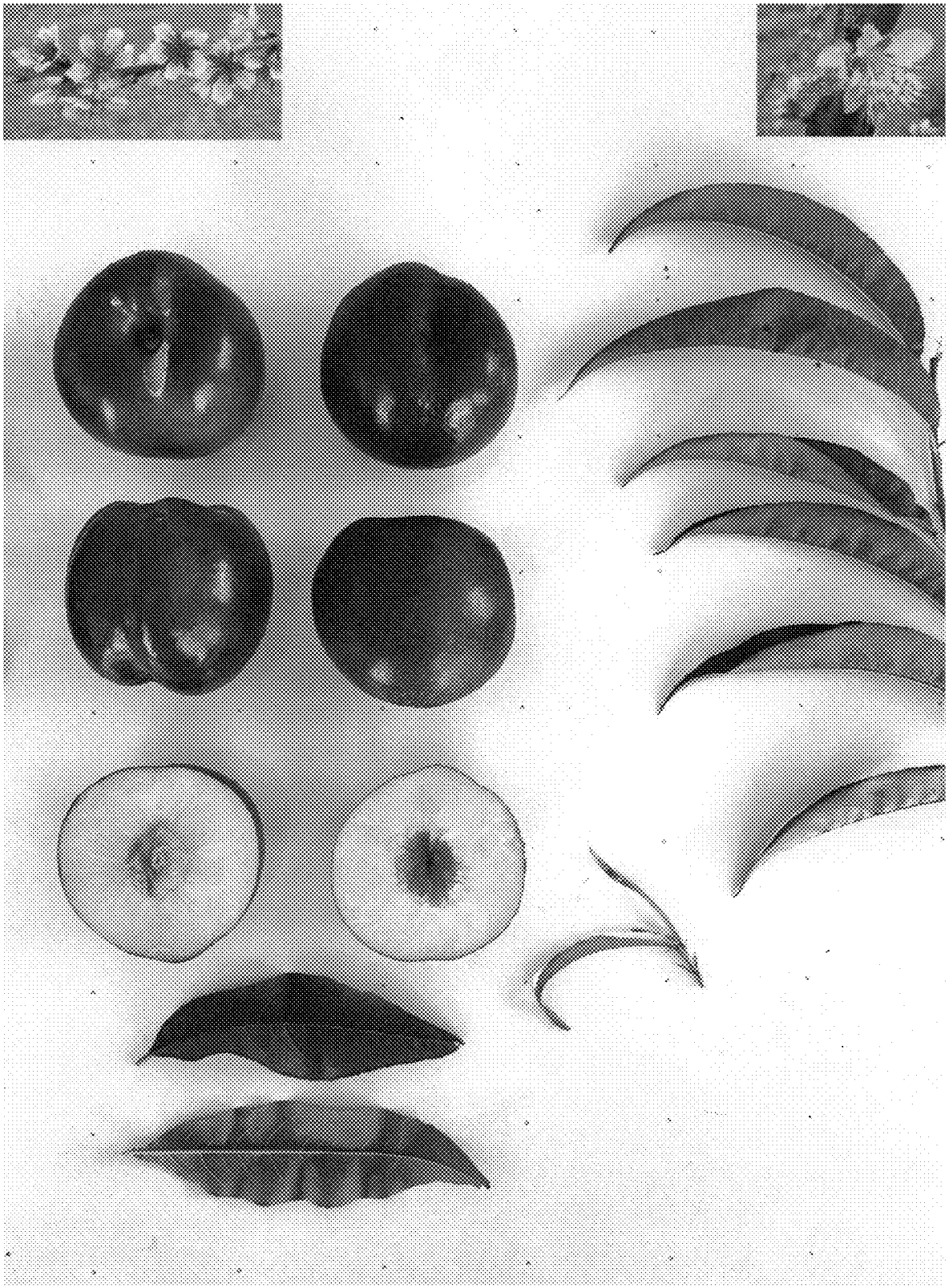

* * * * *